(12) United States Patent
Aoki et al.

(10) Patent No.: US 7,964,626 B2
(45) Date of Patent: Jun. 21, 2011

(54) PROCESS FOR PRODUCING N,N'-CARBONYLDIIMIDAZOLE

(75) Inventors: Yoshikazu Aoki, Yamaguchi (JP); Norimasa Yokoyama, Yamaguchi (JP); Masateru Yasumura, Yamaguchi (JP)

(73) Assignee: Hodogaya Chemical Co., Ltd., Kawasaki-shi (JP)

( * ) Notice: Subject to any disclaimer, the term of this patent is extended or adjusted under 35 U.S.C. 154(b) by 607 days.

(21) Appl. No.: 11/547,524

(22) PCT Filed: Mar. 29, 2005

(86) PCT No.: PCT/JP2005/005891
§ 371 (c)(1),
(2), (4) Date: Sep. 27, 2007

(87) PCT Pub. No.: WO2005/095355
PCT Pub. Date: Oct. 13, 2005

(65) Prior Publication Data
US 2009/0088575 A1    Apr. 2, 2009

(30) Foreign Application Priority Data
Mar. 30, 2004  (JP) ................................. 2004-099257

(51) Int. Cl.
*A61K 31/417* (2006.01)
*C07D 233/60* (2006.01)
(52) U.S. Cl. ..................................... 514/397; 548/341.5
(58) Field of Classification Search ............... 548/341.5; 514/397
See application file for complete search history.

(56) References Cited

U.S. PATENT DOCUMENTS 6,353,115 B1 * 3/2002 Stamm et al. ............. 548/313.7
6,392,057 B1 * 5/2002 Scherer et al. ............ 548/313.7

FOREIGN PATENT DOCUMENTS

| JP | 8 502994 | 4/1996 |
| JP | 2002 503240 | 1/2002 |
| JP | 2002 521474 | 7/2002 |
| WO | 00 02863 | 1/2000 |
| WO | WO 00/14072 A1 | 3/2000 |

* cited by examiner

Primary Examiner — Joseph K. McKane
Assistant Examiner — Janet L Coppins
(74) Attorney, Agent, or Firm — Oblon, Spivak, McClelland, Maier & Neustadt, L.L.P.

(57) ABSTRACT

The present invention provides a process for producing N,N'-carbonyldiimidazole, comprising: reacting phosgene, diphosgene, or triphosgene with imidazole in an inert solvent to produce N,N'-carbonyldiimidazole; to imidazole hydrochloride yielded as a by-product in the above step, adding a gaseous or liquid basic compound represented by the below-shown general formula (1) in an inert solvent to conduct neutralization reaction; and circulating the imidazole thus generated to use it as a starting material for N,N'-carbonyldiimidazole production.

In the general formula (1), $R^1$, $R^2$, and $R^3$ each independently represents a hydrogen atom, a methyl group, or an ethyl group. The CDI produced by the production process of the invention is a compound useful in the fields of synthesis of pharmaceutical agents, synthesis of agricultural chemicals, peptide synthesis, and the like, e.g., intermolecular condensation reactions, intramolecular condensation reactions for synthesizing N-carboxylic anhydrides, production of activated esters, and the like. The compound is especially suitable for use in applications where colorlessness is required.

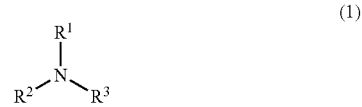

(1)

10 Claims, No Drawings

PROCESS FOR PRODUCING N,N'-CARBONYLDIIMIDAZOLE

TECHNICAL FIELD

The present invention relates to a process for producing N,N'-carbonyldiimidazole. More specifically, it relates to a process for producing N,N'-carbonyldiimidazole by a reaction of imidazole with phosgene or a polymer thereof in an inert solvent, wherein imidazole generated by a neutralization reaction between imidazole hydrochloride yielded as a by-product and a gaseous or liquid basic compound is circulated and used as a starting material for N,N'-carbonyldiimidazole production.

BACKGROUND ART

N,N'-Carbonyldiimidazole (hereinafter abbreviated to CDI) is a useful compound used in the fields of synthesis of pharmaceutical agents, synthesis of agricultural chemicals, peptide synthesis, and the like, e.g., intermolecular condensation reactions, intramolecular condensation reactions for synthesizing N-carboxylic anhydrides, production of activated esters, and the like. The most general synthetic method of CDI is a method of reacting imidazole with phosgene in an inert solvent, which is contrived by H. A. Staab. In this method, as shown in the below-shown chemical formula, a half of the imidazole is utilized as a capture agent for hydrogen chloride generated during the reaction and is separated and removed from CDI after completion of the reaction.

[Chemical formula 1]

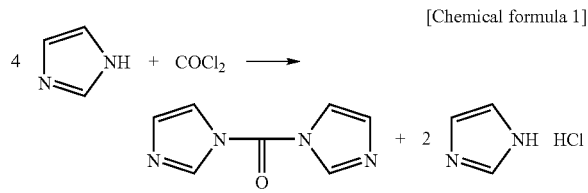

For the purpose of utilizing a whole amount of imidazole, there is disclosed a method of using an organic base as a capture agent for hydrochloric acid generated (e.g., Patent Documents 1 and 2). Moreover, a method of silylating imidazole with a silylating agent such as trimethylsilyl chloride has been performed so that hydrochloric acid is not generated. However, in the case of using an organic base, since the organic base is not completely inactive to phosgene, impurities tend to be produced and remain in the product CDI, the presence of the impurities being a factor of purity decrease. In the case of silylating imidazole, a silylating agent can be circulated and utilized with suppressing generation of hydrochloric acid but it is necessary to make associating capital investment for special handling of the silylating agent which is not generally stable. These methods mentioned above are difficult to utilize as industrial processes for obtaining highly pure CDI at a low cost.

Therefore, there has been used a method of neutralizing the imidazole hydrochloride yielded as a by-product with an inorganic base such as sodium hydroxide or an aqueous solution thereof, recovering the imidazole, and returning it as a starting material for CDI production (e.g., Patent Documents 3 and 4). However, also in the method, when the imidazole is recovered using water as a solvent, labor and cost are required for extraction with an organic solvent immiscible with water since imidazole is soluble in water. Furthermore, even when the imidazole is recovered using an organic solvent, since CDI is severely highly hydrolyzable, it is necessary to incorporate a step of removing water generated during the neutralization reaction.

Patent Document 1: WO98/31672 pamphlet
Patent Document 2: WO00/02863 pamphlet
Patent Document 3: WO00/14072 pamphlet
Patent Document 4: WO00/06551 pamphlet

DISCLOSURE OF THE INVENTION

Problems that the Invention is to Solve

As mentioned above, in the industrial processes for producing CDI, the removal of hydrogen chloride yielded as a by-product during the reaction is a big problem. Thus, it has been desired to develop a process for easily recovering and re-using imidazole from imidazole hydrochloride without involving water formation when imidazole is used as a starting material and also as a capture agent for hydrogen chloride. Moreover, it is always required that CDI produced has little coloration and hence it has also desired to develop a process for producing CDI without requiring any special step for removing coloration.

Means for Solving the Problems

The present inventors have extensively studied for solving the above problems. As a result, they have found that the imidazole hydrochloride yielded as a by-product in the reaction can be dissolved or dispersed in an organic solvent and neutralized with a gaseous or liquid basic compound and, after removal of a neutralization product, imidazole generated can be easily recycled as a starting material for CDI production. Thus, they have accomplished the invention.

Namely, the invention relates to a process for producing N,N'-carbonyldiimidazole, comprising:

reacting phosgene, diphosgene, or triphosgene with imidazole in an inert solvent to produce N,N'-carbonyldiimidazole;

to imidazole hydrochloride yielded as a by-product in the above step, adding a gaseous or liquid basic compound represented by the general formula (1) in an inert solvent to conduct neutralization reaction; and circulating the imidazole thus generated to use it as a starting material for N,N'-carbonyldiimidazole production:

[Chemical formula 2]

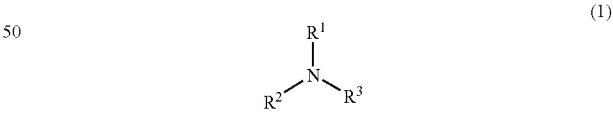

(1)

wherein $R^1$, $R^2$, and $R^3$ each independently represents a hydrogen atom, a methyl group, or an ethyl group.

Moreover, the invention also relates to each of the followings:

The process for producing N,N'-carbonyldiimidazole, wherein the basic compound represented by the general formula (1) is a gaseous ammonia or a liquid ammonia;

The process for producing N,N'-carbonyldiimidazole, wherein the inert solvent is one member or a mixture of two or more members selected from linear ethers, cyclic ethers, and linear esters;

The process for producing N,N'-carbonyldiimidazole, wherein the inert solvent is tetrahydrofuran;

The process for producing N,N'-carbonyldiimidazole, wherein the imidazole generated by the neutralization reaction of the imidazole hydrochloride yielded as a by-product with the basic compound represented by the general formula (1) is taken out as a solid by crystallization or solvent removal and is circulated to use it as a starting material for N,N'-carbonyldiimidazole production;

The process for producing N,N'-carbonyldiimidazole, wherein the imidazole generated by the neutralization reaction of the imidazole hydrochloride yielded as a by-product with the basic compound represented by the general formula (1) is circulated to use it as a starting material for N,N'-carbonyldiimidazole production, in the form of a solution in an inert solvent or a dispersion slurry in an inert solvent without incorporation of a moisture-removing step;

The process for producing N,N'-carbonyldiimidazole, wherein the neutralization reaction of the imidazole hydrochloride yielded as a by-product with the basic compound represented by the general formula (1) is conducted in an inert solvent, hydrochloride salt of the basic compound is removed by filtration, and the imidazole thus generated is circulated to use it as a starting material for N,N'-carbonyldiimidazole production, as it is in the form of a solution in the inert solvent or a dispersion slurry in the inert solvent without incorporation of a moisture-removing step; and The process for producing N,N'-carbonyldiimidazole, wherein the imidazole generated by the neutralization reaction of the imidazole hydrochloride yielded as a by-product with the basic compound represented by the general formula (1) and imidazole newly supplied are mixed in an arbitrary ratio and the resulting mixture is used as a starting material for N,N'-carbonyldiimidazole production.

In the invention, imidazole hydrochloride is neutralized with an organic base and is neutralized without water generation which occurs in the case of neutralization with an inorganic base. Moreover, the basic compound represented by the general formula (1) is inexpensive and is easy to handle. Furthermore, the basic compound represented by the general formula (1) has a low boiling point and hence can be easily removed by boiling or bubbling with an inert gas even when the basic compound represented by the general formula (1) remains in the system after completion of the neutralization reaction, so that any adverse effect owing to the remaining basic compound is not induced in the CDI synthesis through utilization of recycled imidazole.

The hydrochloride of the basic compound represented by the general formula (1) yielded during the neutralization reaction is removed by filtration. The imidazole neutralized into a free form can be circulated and used as a starting material for CDI production as it is or after taken out as a solid after removal of the solvent by evaporation, without incorporation of a moisture-removing step. In the case that it is circulated and used in a solution state, the imidazole formed is used in the form of a solution in an inert solvent or as a dispersion slurry in an inert solvent. In that case, it is also possible that the neutralization reaction of the imidazole hydrochloride yielded as a by-product with the basic compound represented by the general formula (1) is conducted in an inert solvent, the hydrochloride of the basic compound is removed by filtration, and the imidazole generated is circulated and used as it is in the form of a solution of the inert solvent or as a dispersion slurry of the inert solvent.

As the solvent for use in the production of N,N'-carbonyldiimidazole by reacting phosgene, diphosgene, or triphosgene with imidazole, any solvent may be used as far as the solvent is an inert solvent which does not react with phosgene and the hydrogen chloride yielded as a by-product. Moreover, even when the solvent is reactive with them in some degree, it is also possible to use such a solvent since the reaction of imidazole with phosgene and the reaction of imidazole with hydrogen chloride are predominant.

In consideration of removing a minute amount of colored impurities yielded during the reaction, it is preferred to use one member or a mixture of two or more members selected from linear ethers, cyclic ethers, and linear esters. More preferred is tetrahydrofuran. In this case, the reason why the removal of a minute amount of the colored impurities is accurately conducted is considered that linear ethers, cyclic ethers, and linear esters have a high solubility toward a minute amount of the colored impurities. In the invention, the meanings of use of these linear ethers, cyclic ethers, and linear esters as solvents include not only use of these solvents but also methods of using mixtures of aromatic solvents which have hitherto been used as solvents for CDI production and these linear ethers, cyclic ethers, and linear esters.

ADVANTAGE OF THE INVENTION

According to the production process of the invention, the imidazole hydrochloride yielded as a by-product at CDI production is subjected to a neutralization reaction by adding a gaseous or liquid inexpensive basic compound easy to handle, whereby imidazole can be recovered in a free state without water generation. Thereafter, it becomes possible to circulate the imidazole inexpensively and easily without incorporating steps of extraction, azeotropic dehydration, and the like. Moreover, according to the production process of the invention, CDI with little coloration can be obtained as compared with conventional production processes.

BEST MODE FOR CARRYING OUT THE INVENTION

The following will explain the invention in detail.

As the imidazole hydrochloride for use in the invention, it is preferred to use the imidazole hydrochloride yielded as a by-product at CDI production when the purpose of the invention is considered but imidazole hydrochloride separately synthesized and imidazole hydrochloride yielded as a by-product at production of the other compounds.

The basic compound for use in the invention is not particularly limited as far as it is a compound represented by the general formula (1), wherein $R^1$, $R^2$, and $R^3$ each independently represents a hydrogen atom, a methyl group, or an ethyl group. As specific compounds, there may be mentioned ammonia, methylamine, dimethylamine, trimethylamine, ethylamine, diethylamine, triethylamine, methyldiethylamine, and ethyldimethylamine. In particular, ammonia is preferably used.

The inert solvent is not particularly limited as far as it is an organic solvent which does not inhibit reactions of imidazole with phosgenes and the neutralization reaction of imidazole hydrochloride. As specific examples of the inert solvent to be used in the invention, there may be mentioned cyclic ethers such as tetrahydrofuran and dioxane; linear ethers such as diisopropyl ether and dibutyl ether; halogenated hydrocarbons such as dichloromethane, chloroform, and trichloroethane; aromatic hydrocarbons such as toluene, xylene, and chlorobenzene; linear esters such as ethyl acetate and butyl acetate; ketones such as acetone and methyl isobutyl ketone; nitriles such as acetonitrile; and aliphatic hydrocarbons such as hexane and heptane. Preferred are linear ethers, cyclic ethers, and linear esters and particularly preferred is tetrahydrofuran. Moreover, these organic solvents may be used singly or as a mixture of two or more thereof.

The neutralization reaction of the imidazole hydrochloride with the gaseous or liquid basic compound in the production process of the invention is preferably conducted by dissolving or dispersing the imidazole hydrochloride in an inert solvent and introducing the basic compound. Alternatively, there is also a method wherein the imidazole hydrochloride is added into the inert solvent in which a basic compound is dissolved or the imidazole hydrochloride dissolved or dispersed in the inert solvent is poured thereinto.

The basic compound for use in the neutralization of the imidazole hydrochloride is used in an amount of 1 to 10 molar equivalents to the imidazole hydrochloride. Preferred is the use in an amount of 1 to 5 molar equivalents. The inert solvent for use in the neutralization of the imidazole hydrochloride is used in an amount by weight 1 to 20 times the weight of the imidazole hydrochloride. Preferred is the use in an amount by weight 3 to 5 times.

The neutralization reaction of the imidazole hydrochloride with the gaseous or liquid basic compound is conducted usually at 0 to 100° C., preferably at 20 to 50° C. The reaction time is conducted usually for 0.5 to 20 hours, preferably for 2 to 8 hours. The reaction is preferably conducted in an atmosphere of an inert gas such as nitrogen or argon under an anhydrous condition but the atmospheric condition is not particularly limited.

The reaction liquid after completion of the neutralization reaction is subjected to filtration of a neutralization product at any temperature, and the filtration is preferably conducted in an atmosphere of an inert gas under an anhydrous condition but the atmospheric condition is not particularly limited. The filtrate containing imidazole recovered is used as a starting material for CDI production as it is or after concentration. Furthermore, the imidazole is taken out as a solid by an operation such as crystallization and is used as a starting material for CDI production The neutralized and recovered imidazole is dissolved or dispersed in an inert solvent and then a CDI-synthesizing reaction is conducted by introducing a predetermined amount of phosgene, diphosgene, or triphosgene. At this time, the reaction may be conducted with increasing a unit yield of CDI by adding new imidazole to the neutralized and recovered imidazole.

The following will explain the invention further in detail with reference to Examples but the invention is not limited to the following Examples.

Example 1

Synthesis of CDI and by-Product Imidazole Hydrochloride Using New Imidazole

To a 1000 ml flask were added 108.3 g (1.59 mol) of imidazole and 630 g of tetrahydrofuran. After the atmosphere of the system was replaced with nitrogen, the imidazole was dissolved under stirring. Thereto was added dropwise 39.3 g (0.2 mol) of diphosgene at room temperature over a period of 2 hours. After completion of the dropwise addition, the stirring was continued at room temperature for 1 hour and then the whole was heated to 55° C., followed by continuous stirring for another 1 hour. Imidazole hydrochloride yielded as a by-product was filtrated with heat and was then washed with 100 g of tetrahydrofuran. The imidazole hydrochloride filtrated off was dried under reduced pressure at 40° C. to obtain 83.2 g (0.796 mol) of imidazole hydrochloride (recovery of 100%).

A filtrate containing CDI was concentrated and subjected to toluene-crystallization, and CDI was filtrated off under a nitrogen atmosphere. The CDI filtrated off was dried under reduced pressure at 40° C. to obtain 58.0 g (0.358 mol) of CDI as white crystals (yield 90%). M.p. 111.2 to 118.6° C.

Example 2

Neutralization and Recovery of Imidazole by Neutralization Reaction of Imidazole Hydrochloride Into a 500 ml flask were added 83.0 g (0.794 mol) of the imidazole hydrochloride obtained in Example 1 and 274 g of tetrahydrofuran. After the atmosphere of the system was replaced with nitrogen, the imidazole hydrochloride was dispersed under stirring. Ammonia gas was introduced thereinto in an amount of 25 l (1.12 mol) at a temperature of 30 to 40° C. over a period of 4 hours. After introduction of ammonia gas, stirring was continued at 35° C. for 1 hour. After the reaction liquid was cooled to room temperature, ammonium chloride as a neutralization product was filtrated off and then washed with 54 g of tetrahydrofuran. The filtrate was concentrated and 150 g of tetrahydrofuran was removed by evaporation to obtain 185.4 g of tetrahydrofuran containing neutralized and recovered imidazole. As a result of gas chromatography and neutralization titration analysis, it was found that it contained 48.6 g (0.714 mol) of imidazole (recovery 90%). M.p. 82 to 88° C.

Example 3

Synthesis of CDI with Neutralized and Recovered Imidazole

Into a 500 ml flask were added the tetrahydrofuran containing 48.1 g (0.707 mol) of imidazole obtained in Example 2 and 140 g of tetrahydrofuran. After the atmosphere of the system was replaced with nitrogen, 18.5 g (0.094 mol) of diphosgene was added dropwise at room temperature over a period of 2 hours. Thereafter, the same operations as in Example 1 were conducted and white crystals of CDI were taken out. Yield 24.4 g (0.15 mol) (percent yield 85%). M.p. 111.3 to 116.9° C.

While the invention has been described in detail and with reference to specific embodiments thereof, it will be apparent to one skilled in the art that various changes and modifications can be made therein without departing from the spirit and scope thereof.

The present application is based on Japanese Patent Application No. 2004-099257 filed on Mar. 30, 2004, and the contents are incorporated herein by reference.

INDUSTRIAL APPLICABILITY

The CDI produced by the production process of the invention is a compound useful in the fields of synthesis of pharmaceutical agents, synthesis of agricultural chemicals, peptide synthesis, and the like, e.g., intermolecular condensation reactions, intramolecular condensation reactions for synthesizing N-carboxylic anhydrides, production of activated esters, and the like. It is especially suitable for use in applications where colorlessness is required.

The invention claimed is:
1. A process for producing N,N'-carbonyldiimidazole, comprising:
reacting phosgene, diphosgene, or triphosgene with imidazole in an inert solvent to produce N,N'-carbonyldiimidazole;
to imidazole hydrochloride yielded as a by-product in the above step, adding a gaseous or liquid basic compound represented by the below-shown general formula (1) in an inert solvent to conduct neutralization reaction; and
circulating the imidazole thus generated to use it as a starting material for N,N'-carbonyldiimidazole production:

[Chemical formula 3]

(1)

wherein $R^1$, $R^2$, and $R^3$ each independently represents a hydrogen atom, a methyl group, or an ethyl group.

2. A process for producing N,N'-carbonyldiimidazole comprising:
reacting phosgene, diphosgene, or triphosgene with imidazole in an inert solvent to produce N,N'-carbonyldiimidazole;
to imidazole hydrochloride yielded as a by-product in the above step, adding a gaseous or liquid basic compound represented by the below-shown general formula (1) in an inert solvent to conduct neutralization reaction; and
circulating the imidazole thus generated to use it as a starting material for N,N'-carbonyldiimidazole production:

[Chemical formula 3]

(1)

wherein $R^1$, $R^2$, and $R^3$ each independently represents a hydrogen atom, a methyl group, or an ethyl group
wherein the basic compound represented by the general formula (1) is a gaseous ammonia or a liquid ammonia.

3. The process for producing N,N'-carbonyldiimidazole according to claim 1 or 2, wherein the inert solvent is one member or a mixture of two or more members selected from linear ethers, cyclic ethers, and linear esters.

4. The process for producing N,N'-carbonyldiimidazole according to any one of claims 1 to 2, wherein the inert solvent is tetrahydrofuran.

5. The process for producing N,N'-carbonyldiimidazole according to any one of claims 1 to 2, wherein the imidazole generated by the neutralization reaction of the imidazole hydrochloride yielded as a by-product with the basic compound represented by the general formula (1) is taken out as a solid by crystallization or solvent removal and is circulated to use it as a starting material for N,N'-carbonyldiimidazole production.

6. The process for producing N,N'-carbonyldiimidazole according to any one of claims 1 to 2, wherein the imidazole generated by the neutralization reaction of the imidazole hydrochloride yielded as a by-product with the basic compound represented by the general formula (1) is circulated to use it as a starting material for N,N'-carbonyldiimidazole production, in the form of a solution in an inert solvent or a dispersion slurry in an inert solvent without incorporation of a moisture-removing step.

7. The process for producing N,N'-carbonyldiimidazole according to any one of claims 1 to 2, wherein the neutralization reaction of the imidazole hydrochloride yielded as a by-product with the basic compound represented by the general formula (1) is conducted in an inert solvent, hydrochloride salt of the basic compound is removed by filtration, and the imidazole thus generated is circulated to use it as a starting material for N,N'-carbonyldiimidazole production, as it is in the form of a solution in the inert solvent or a dispersion slurry in the inert solvent without incorporation of a moisture-removing step.

8. The process for producing N,N'-carbonyldiimidazole according to any one of claims 1 to 2, wherein the imidazole generated by the neutralization reaction of the imidazole hydrochloride yielded as a by-product with the basic compound represented by the general formula (1) and imidazole newly supplied are mixed in an arbitrary ratio and the resulting mixture is used as a starting material for N,N'-carbonyldiimidazole production.

9. The process for producing N,N'-carbonyldiimidazole according to claim 1 or 2, wherein said imidazole hydrochloride is removed by filtration.

10. The process for producing N,N'-carbonyldiimidazole according to claim 1, wherein said imidazole hydrochloride is neutralized without water generation.

* * * * *